United States Patent
Levatino

(10) Patent No.: US 6,997,713 B2
(45) Date of Patent: Feb. 14, 2006

(54) MICROTUBES FOR SURGERY AND DENTISTRY

(76) Inventor: Samuel R. Levatino, 3608 Woodland Ridge Blvd., Baton Rouge, LA (US) 70816

( * ) Notice: Subject to any disclaimer, the term of this patent is extended or adjusted under 35 U.S.C. 154(b) by 198 days.

(21) Appl. No.: 10/605,352

(22) Filed: Sep. 24, 2003

(65) Prior Publication Data

US 2005/0065497 A1 Mar. 24, 2005

(51) Int. Cl.
*A61C 5/00* (2006.01)

(52) U.S. Cl. .................................................. 433/215
(58) Field of Classification Search ............... 433/29, 433/215, 216; 604/272, 264, 506, 164.01, 604/170.02, 239
See application file for complete search history.

(56) References Cited

U.S. PATENT DOCUMENTS

| | | | |
|---|---|---|---|
| 4,029,104 A | 6/1977 | Kerber | 128/348 |
| 4,418,688 A | 12/1983 | Loeb | 128/6 |
| 4,619,274 A | 10/1986 | Morrison | 128/772 |
| 4,722,724 A | 2/1988 | Shock | 604/8 |
| 4,909,796 A | 3/1990 | Hagio et al. | 604/247 |
| 4,917,670 A | 4/1990 | Hurley et al. | 604/51 |
| 5,074,843 A | 12/1991 | Dalton et al. | 604/68 |
| 5,100,379 A | 3/1992 | Wendell | 604/51 |
| 6,135,769 A * | 10/2000 | Kwan | 433/80 |

\* cited by examiner

*Primary Examiner*—Kevin C. Simmons
(74) *Attorney, Agent, or Firm*—Reginald F. Roberts, Jr.

(57) ABSTRACT

A microtube for surgery and dentistry. The microtube transmits light, pressure, vacuum, or a pharmaceutical agent to the site of a surgical or dental operation or procedure. Because of its extreme microsize and multiple ports, the microtube does not harm tissue, and is especially suited for surgical and dental procedures such as a root canal and operations involving extremely small spaces and limited accessability. A side port at one end of the microtube provides extreme versatility by being capable, by rotation of the microtube about its longitudinal axis, of covering a perimeter of about one hundred and eighty degrees.

2 Claims, 1 Drawing Sheet

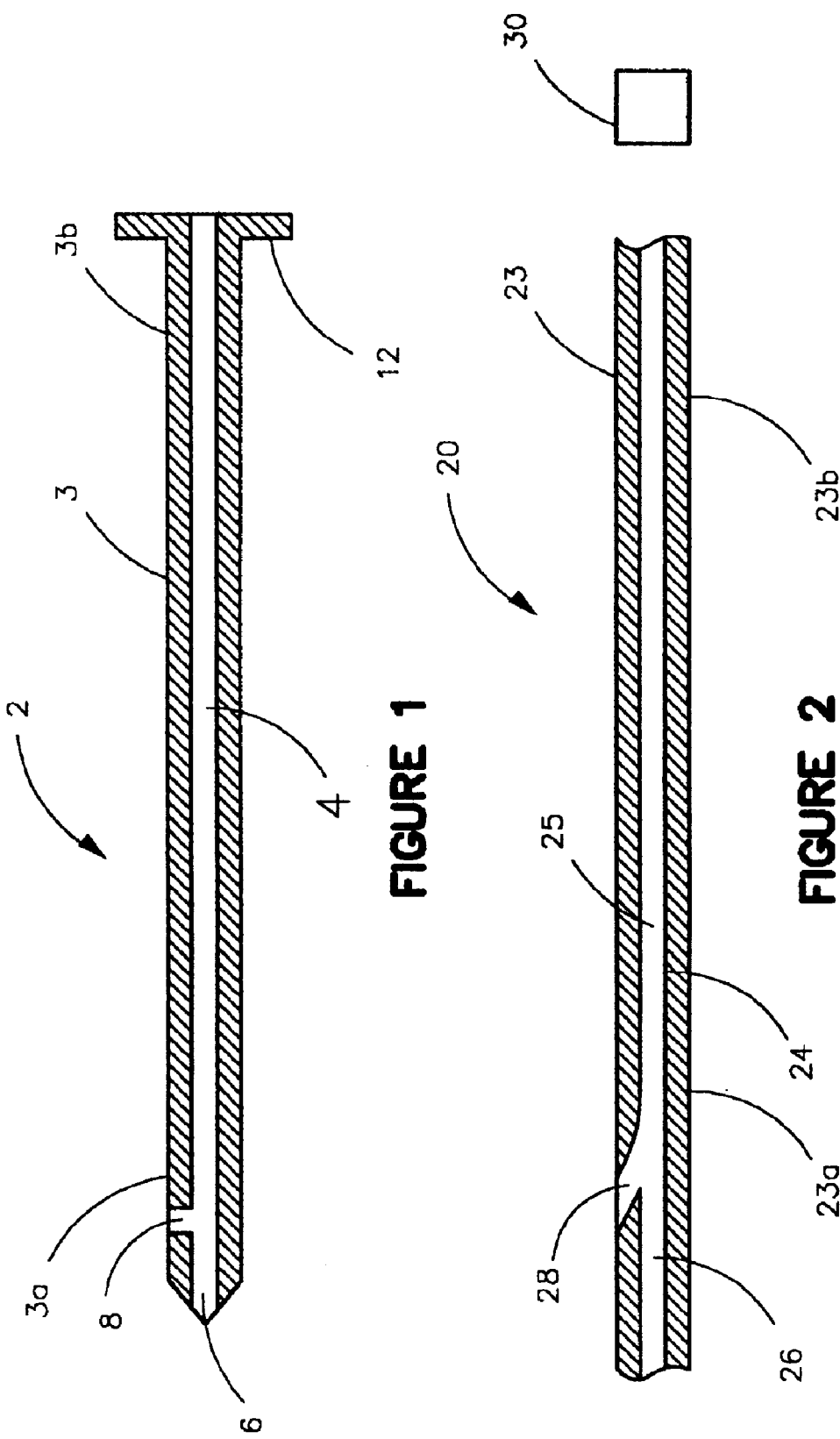

MICROTUBES FOR SURGERY AND DENTISTRY

BACKGROUND OF INVENTION

The present invention relates to the fields of medicine and dentistry. More particularly, the invention relates to microtubes for surgical and dental procedures.

SUMMARY OF INVENTION

In general, the present invention in a first aspect provides a microtube for surgery and dentistry. A first embodiment of the microtube comprises a tubular member having anterior and posterior ends; an interior axial opening extending from the anterior to the posterior end of the tubular member; and a side port disposed at the anterior end of the tubular member, and constructed and arranged for connecting the axial opening to a site of a surgical or dental procedure, and for delivery to the site of a therapeutic agent to be used for the surgical or dental procedure.

A second embodiment of the microtube comprises a tubular member having anterior and posterior ends; a port disposed at the anterior end of the tubular member; and an inner core of a material capable of transmitting a laser beam, the inner core extending from the posterior end through the port at the anterior end of the tubular member.

In a second aspect, the invention provides a method for transmitting a therapeutic agent to a site of a surgical or dental procedure. The method comprises (a) providing a microtube comprising a tubular member having anterior and posterior ends; an interior axial opening extending from the anterior to the posterior end of the tubular member; and a port disposed at the anterior end of the tubular member, and constructed and arranged for connecting the axial opening to the site of the surgical or dental procedure, and for delivery to the site of the therapeutic agent to be used for the surgical or dental procedure; (b) connecting the port of the tubular member to the site of the surgical or dental procedure; (c) connecting the axial opening at the posterior end of the tubular member to the source of the therapeutic agent; and (d) delivering the therapeutic agent to the site of the surgical or dental procedure.

In a third aspect, the invention provides an improved procedure for a root canal. Current dental practice for carrying out a root canal comprises drilling, mechanical canal debridement, and chemical canal debridement. The improvement comprises (a) providing a microtube comprising a tubular member having anterior and posterior ends; a side port disposed at the anterior end of the tubular member, and an inner core of a material capable of transmitting a laser beam, the inner core extending from the posterior end through the port at the anterior end of the tubular member; (b) disposing the side port of the tubular member at the site of the root canal; (c) disposing the axial opening at the posterior end of the tubular member at the source of the laser beam; and (d) delivering the laser beam through the port to the site of the root canal, thereby combining the mechanical canal debridement and the chemical debridement into a single procedure, enabling removal of pulpal tissue in three-dimensional volume elements which files and other instruments cannot reach, and sterilizing the canal and ablating the pulpal tissue.

BRIEF DESCRIPTION OF DRAWINGS

FIG. 1 is a schematic representation of a first embodiment of a microtube for surgery and dentistry, made in accordance with the principles of the present invention.

FIG. 2 is a schematic representation of a second embodiment of a microtube for surgery and dentistry, made in accordance with the principles of the present invention.

DETAILED DESCRIPTION

More specifically, reference is made to FIG. 1, in which is shown a first embodiment of a microtube for surgery and dentistry, made in accordance with the principles of the present invention, and generally designated by the numeral 2.

The microtube 2 comprises a tubular member 3 having anterior and posterior ends 3a and 3b, respectively; an interior axial opening 4; and front and side ports 6 and 8, respectively, constructed and arranged for connecting the axial opening to a site of a surgical or dental procedure, and for delivery to the site of a therapeutic agent 10a being used for the surgical or dental procedure. Instead of a single axial opening a plurality of openings may be utilized, and are often beneficial. The posterior end 3b of the tubular member 3 is provided with means 12 for connecting the microtube 2 to a source 10 of the therapeutic agent 10a. The microtube 2 has an outside diameter (o.d.) of from about ten to about one hundred microns, and an inside diameter (i.d.) of from about five to about fifty microns. These dimensions are critical for optimum functioning of the microtube 2. Preferably, the microtube 2 has a length of from about twenty to about twenty-five millimeters.

During the surgical or dental procedure, the microtube 2 is connected to the source 10 of the therapeutic agent 10a, which is generally pressure, vacuum, or a pharmaceutical agent, and the therapeutic agent 10a is transmitted through the microtube 2 to the site of the surgical or dental procedure via the axial opening 4 and or or both ports 6 and/or 8.

The pharmaceutical agent is usually an antibiotic, a chemotherapeutic agent, or a sealant. The length of the microtube 2 is preferably from about twenty to about twenty-five millimeters, but the length is not critical.

Because of its extreme microsize, which is critical, the microtube 2 does not harm tissue when used to transmit pressure, vacuum, or pharmaceuticals to the site being operated upon, and is especially suited for surgical and dental procedures such as a root canal and surgical operations involving extremely limited space.

Because of the provision of front and side ports, the microtube 2 provides versatility in enabling the surgeon, dentist, or oral surgeon to reach various areas of limited accessibility at the site of the surgical or dental procedure.

The combination of multiple ports disposed perpendicularly to one another, and of the extremely small dimensions of the microtube 2, the microtube 2 provides a unique instrument for surgeons, dentists, and oral surgeons performing operations in a space limited both in area and in accessibility.

Reference is now made to FIG. 2, in which is shown a second embodiment of a microtube for surgery and dentistry, made in accordance with the principles of the present invention, and generally designated by the numeral 20.

The microtube 20 comprises a tubular member 23 having anterior and posterior ends 23a and 23b, respectively; an interior axial opening 24; front and side ports 26 and 28, respectively; and an inner core 25 of a material capable of transmitting a laser beam from a source 30, the inner core 25 extending from the posterior end 23b through the ports 26 and 28 at the anterior end 23a of the tubular member 23. The dimensions of the microtube 20 are the same as those of the microtube 2.

The microtubes 2 and 20 comprise a metal tube made by metallic electrodeposition. The side ports 8 and 28 provide extreme versatility by virtue of their being capable, by rotation of the microtubes 2 and 20 about their longtitudinal axes, of dispsosing the ports 8 and 28 in a perimeter of about one hundred and eighty degrees.

A particularly important application of the present invention is the provision of an improved procedure for doing a root canal. Use of the microtube 20 as a side-firing laser tube combines mechanical canal debridement and chemical canal debridement into a single procedure. It is presently virtually impossible to clean thoroughly a root-canal system with instruments alone. The use of chemical debridement enables removal of vital and/or nonvital pulpal tissue in three-dimensional volume elements which files and conventional instruments cannot reach. A couple of passes of the side-firing laser tube 20 to the apex of the tooth will clean, debride, and sterilize the site to a greater extent than any existing combination of state-of-the-art procedures. The side-firing laser tube 20 is so small that it will go all the way down to the apex of the tooth without the need for canal enlargement. It will then sterilize the canal and ablate all pulpal tissue. Obturation is accomplished with a modified hydrophilic mineral trioxide aggregate canal sealant delivered through side 8 and/or front 6 ports of the microtube 2.

Because both the focal length and the wavelength of the laser beam are adjustable, the beam is capable of ablating diseased tissue in conformity with the focal length that is set. This can be done without harm to non-diseased, healthy tissue in very hard-to-reach, relatively inaccessible areas. Such areas cannot be reached or accessed with and by an instrument as small as the smallest needle probe. This microtube laser technology enables early surgery, limited only by early diagnosis.

While certain embodiments and details have been described to illustrate the principles of the present invention, it will be apparent to those skilled in the art that many modifications are possible without departing from the spirit and scope of the invention.

I claim:

1. In a dental method for a root canal comprising drilling a tooth, mechanical canal debridement, and chemical canal debridement, the improvement comprising the steps of:

(a) providing a microtube comprising a tubular member having anterior and posterior ends, an outside diameter of from about ten to about one hundred microns, and an inside diameter of from about five to about fifty microns, the tubular member being fabricated by metallic electrodeposition; a side port disposed at the anterior end of the tubular member; and an inner core of a material capable of transmitting a laser beam, the inner core extending from the posterior end through the side port at the anterior end of the tubular member;

(b) disposing the side port of the tubular member at the site of the root canal;

(c) disposing an axial opening at the posterior end of the tubular member at a source of the laser beam; and (d) delivering the laser beam through the side port of the tubular member to the site of the root canal, thereby combining the mechanical canal debridement and the chemical canal debridement into a single procedure, enabling removal of pulpal tissue in three-dimensional volume elements which files and other instruments cannot reach, and sterilizing the canal and ablating the pulpal tissue.

2. The dental method of claim 1, further comprising the steps of:

(e) providing a microtube comprising a tubular member having anterior and posterior ends, an outside diameter of from about ten to about one hundred microns, and an inside diameter of from about five to about fifty microns, the tubular member being fabricated by metallic electroden position; an interior axial opening extending from the anterior to the posterior end of the tubular member; and a port disposed at the anterior end of the tubular member, and constructed and arranged for connecting the axial opening to a site of a surgical or dental procedure, and for delivering to the site a therapeutic agent to be used for the surgical or dental procedure; and (f) delivering through the port of the tubular member to the site of the root canal a sealant, thereby obturating the tooth at the site of the root canal.

* * * * *